United States Patent

Dach et al.

[11] Patent Number: 5,510,484
[45] Date of Patent: Apr. 23, 1996

[54] PROCESS FOR PREPARING 1,3-DIMETHY-4,5-DIAMINOURACIL

[75] Inventors: Rolf Dach, Gau-Algesheim; Wilfried Goldschmidt, Ingelheim am Rhein, both of Germany

[73] Assignee: Boehringer Ingelheim KG, Ingelheim am Rhein, Germany

[21] Appl. No.: 225,011

[22] Filed: Apr. 7, 1994

[30] Foreign Application Priority Data

Apr. 7, 1993 [DE] Germany ............... 43 11 538.1

[51] Int. Cl.$^6$ ............... C07D 239/02
[52] U.S. Cl. ............... 544/311
[58] Field of Search ............... 544/311

[56] References Cited

U.S. PATENT DOCUMENTS

| | | | |
|---|---|---|---|
| 2,646,432 | 7/1953 | Homeyer | 544/311 |
| 3,929,788 | 12/1975 | Miller | 544/311 |
| 3,946,012 | 3/1976 | Takino et al. | 544/311 |
| 4,120,947 | 10/1978 | Diamond | 544/311 |
| 4,546,182 | 10/1985 | Kjellin et al. | 544/267 |
| 5,321,029 | 6/1994 | Maschler et al. | 544/267 |

FOREIGN PATENT DOCUMENTS

| | | | |
|---|---|---|---|
| 2831037 | 2/1979 | Germany | 544/311 |
| 37999 | 9/1981 | Japan | 544/311 |
| 662550 | 5/1979 | U.S.S.R. | 544/311 |
| 2001310 | 1/1979 | United Kingdom . | |

OTHER PUBLICATIONS

N. A. Frolova et al. Khim–Farm Zh. 22(1) (1988) 67.
Chemical Abstracts, vol. 109, No. 9, 1988—"Catalytic Reduction of 1,3—Dimethyl—4—Amino—5 Nitrosouracil: Process Design", Abstract #733924.

*Primary Examiner*—Cecilia Tsang
*Attorney, Agent, or Firm*—Robert P. Raymond; Wendy E. Rieder; Mary-Ellen M. Devlin

[57] ABSTRACT

The present invention relates to an improved process for preparing 1,3-dimethyl-4,5-diaminouracil by catalytic reduction of 1,3-dimethyl-4-amino-5-nitrosouracil in the presence of a palladium/charcoal catalyst.

3 Claims, No Drawings

PROCESS FOR PREPARING 1,3-DIMETHY-4,5-DIAMINOURACIL

The present invention relates to an improved process for preparing 1,3-dimethyl-4,5-diaminouracil (I)

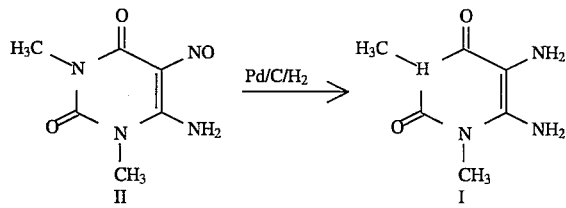

The basic structure of 4,5-diaminouracil (I) constitutes a major component in the syntheses of purine derivatives, such as theophylline, caffeine or theobromine.

Some of these purine derivatives have valuable pharmacological properties. For example, theophylline is known to be effective in the treatment of bronchial asthma, and increases cardiac performance and blood circulation through the coronary blood vessels. Theophylline thus belongs to a group of highly effective cardiac drugs, and can also act as a diuretic.

The starting component for synthesis of theophylline consists of 1,3-dimethyl-4,5-diaminouracil (I) which can easily be converted into theophylline, e.g. with formic acid.

In view of the great need for this purine derivative and its use as an active substance in pharmaceuticals, there is considerable interest in making this product available in high yields and with a good quality, i.e., primarily in highly pure form.

Processes for reducing 1,3-dimethyl-4-amino-5-nitrosouracil (II) to obtain 1,3-dimethyl-4,5-diaminouracil are known from the prior art. Thus, for hydrogen sulphide in liquid ammonia [H. Krahnefeld, J. Wolf, S. Stutzriemer, H. Zumpe, K. D. Fritsche and G. Hockeborn, DD 212,253].

Corresponding reduction by the electrolytic method is also known [A. N. Dolgachev, Avrutskaja and Y. M. Fioshin, Elektrokhimiya 15(12) (1979) 1882].

It is also known to carry out catalytic reduction of 1,3-dimethyl-4-amino-5-nitrosouracil (II) to obtain 1,3-dimethyl-4,5-diaminouracil (I) using palladium catalysts [N. A. Frolova, Z. A. Yugai, K. M. Makhkamov and E. A. Sapozhnikova, Khim.-Farm. Zh. 22(1) (1988) 67].

All the methods of synthesis described are either unsuitable for production of the diaminouracil derivative on an industrial scale or can only be used with major restrictions.

Thus, N. A. Frolova et al. report that the use of a palladium/charcoal catalyst for large-scale industrial purposes involves some variations in the product yield and the product quality and that the foaming which occurs during the reaction presents practical problems.

It has now been found, surprisingly, that the use of a palladium/charcoal catalyst makes it possible to obtain 1,3-dimethyl-4,5-diaminouracil (I) in quantitative yields and with a high degree of purity, if certain reaction conditions are adhered to. The quality characteristics of the reduction product are so good that, as a result, it can be further processed directly into theophylline or the calcium salt thereof, without isolation and further purification of the 1,3-dimethyl-4,5-diaminouracil (I) or the so-called formyl body thereof. A further advantage of the process according to the invention is that the hydrogenation can be carried out in suspension, thus enabling hydrogenation to be performed at low temperatures.

In order to do this, an aqueous suspension of the 1,3-dimethyl-4-amino-5-nitrosouracil (II) is mixed with a palladium/charcoal catalyst, preferably having a palladium content of about 5%. In the resulting suspension, at the start of the reaction, the pH is adjusted to a level in the range from 7 to 10, preferably from 8 to 9.5 and most preferably to pH 9, using an aqueous solution of a compound which has an alkaline reaction, preferably an aqueous solution of an alkali metal hydroxide and most preferably with concentrated sodium hydroxide solution.

The suspension thus treated is then hydrogenated under hydrogen pressure in the range from 1 to 20 bar, preferably 2 to 6 bar, and more preferably under a hydrogen pressure of 3 bar, at a temperature in the range from 20° to 60° C. and preferably in the range from 30° to 50° C. After the uptake of hydrogen has ended, the suspension is heated to a temperature in the range from 15° to 40° C., preferably 20° to 30° C., and formic acid is added until all the 1,3-dimethyl-4,5-diaminouracil (I) in the form of the formate has gone into solution. The catalyst can then be separated from the resulting reaction solution, expediently by filtration. HPLC analysis of the filtrate confirms that the 1,3-dimethyl-4,5-diaminouracil (I) has reacted to a level of 99.9%, based on the 1,3-dimethyl-4-amino-5-nitrosouracil (II) used. Formic acid is again added to the filtrate thus obtained and the reaction mixture is left to react at a temperature of about 85° C. over a period of about 40 minutes and then the calcium salt of the theophylline is precipitated with calcium hydroxide suspension. The theophylline-calcium is filtered off, washed with water and dried at a temperature of about 60° C.

The invention described will now be illustrated by means of the process described in the Examples. Various other embodiments of the process will be apparent from this description to anyone skilled in the art. However, it is expressly pointed out that the Example and specification are provided solely as illustrations and must not be regarded as restricting the invention.

EXAMPLE 1

254 g (81 nmol) of 1,3-dimethyl-4-amino-5-nitrosouracil (41% water content) were combined with 310 ml of water and 17 g of 5% palladium/charcoal catalyst (precipitated by alkaline reaction). Then concentrated sodium hydroxide solution was added to the reaction mixture to adjust the pH to 9. The resulting suspension was hydrogenated under a hydrogen pressure of 3 bar, with stirring, within a temperature range from 30° to 50° C. After the uptake of hydrogen had ceased, the reaction mixture was cooled to a temperature in the range from 20° to 30° C., 40 g (869 mmol) of formic acid were added and the catalyst was then filtered off. A further 25 g (543 mmol) of formic acid were added to the filtrate and the mixture was left to finish reacting at a temperature of 85° C. for a period of about 40 minutes. To the resulting mixture were added 65 g of calcium hydroxide suspension, after which the calcium salt of the theophylline was precipitated. The precipitated calcium salt was filtered off, washed with 200 ml of water and the calcium salt isolated in this way was dried for about 12 hours at 60° C. in a circulating air dryer. In this way, the yield of theophylline calcium was 79%, based on the 1,3-dimethyl-4-amino-5-nitrosouracil used.

What is claimed is:

1. A process for preparing 1,3-dimethyl-4,5-diaminouracil by catalytic reduction of 1,3-dimethyl-4-amino-5-nitrosouracil in the presence of a palladium/charcoal catalyst, characterised in that, in an aqueous suspension, the 1,3-dimethyl-4-amino-5-nitrosouracil is adjusted to a pH in the range from 7 to 10 with an aqueous solution of an alkali compound and subsequently hydrogenation is carried out under a hydrogen pressure in the range from 1 to 20 bar within a temperature range from 20° to 60° C. and after the uptake of hydrogen has ceased, formic acid is added to the reaction mixture at a temperature in the range from 15° to 40° C. until all the 1,3-dimethyl-4,5-diaminouracil has gone into solution, the reaction mixture is filtered off from the catalyst and the 1,3-dimethyl-4,5-diamino-uracil is isolated in the form of the formate thereof.

2. The process according to claim 1, characterised in that, in an aqueous suspension of the 1,3-dimethyl-4-amino-5-nitrosouracil, a pH in the range from 8 to 9.5 is obtained using an aqueous solution of an alkali metal hydroxide and subsequently hydrogenation is carried out under a hydrogen pressure in the range from 2 to 6 bar within a temperature range from 30° to 50° C. and when the uptake of hydrogen has ceased formic acid is added to the reaction mixture at a temperature in the range from 20° to 30° C. until all the 1,3-dimethyl-4,5-diaminouracil has gone into solution, the reaction mixture is filtered off from the catalyst and the 1,3-dimethyl-4,5-diaminouracil is isolated in the form of the formate thereof.

3. The process according to claim 1, characterised in that, in an aqueous suspension of the 1,3-dimethyl-4-amino-5-nitrosouracil, a pH of 9 is obtained using sodium hydroxide solution and subsequently hydrogenation is carried out under a hydrogen pressure of 3 bar within a temperature range from 30° to 50° C. and after the uptake of hydrogen has ceased formic acid is added to the reaction mixture at a temperature in the range from 20° to 30° C. until all the 1,3-dimethyl-4,5-diaminouracil has gone into solution, the reaction mixture is filtered off from the catalyst and the 1,3-dimethyl-4,5 diaminouracil is isolated in the form of the formate thereof.

* * * * *